United States Patent [19]

Ono et al.

[11] Patent Number: 4,751,185

[45] Date of Patent: Jun. 14, 1988

[54] ANALYSIS METHOD FOR HOP BITTERING COMPONENTS

[75] Inventors: Miyoko Ono, Osaka; Youichi Kakudo, Takatsuki; Yasuo Ishida, Mukoh; Suehiro Ueda, Otsu, all of Japan

[73] Assignees: Shimadzu Corporation; Suntory Limited, both of Osaka, Japan

[21] Appl. No.: 907,855

[22] Filed: Sep. 15, 1986

[30] Foreign Application Priority Data

Sep. 13, 1985 [JP] Japan ............................. 60-203992

[51] Int. Cl.$^4$ .................... B01D 15/08; G01N 30/02; G01N 33/14
[52] U.S. Cl. ...................................... 436/24; 436/161; 73/61.1 C; 210/656; 426/231
[58] Field of Search .................... 436/24, 161; 422/70; 426/231, 424, 600; 73/61.1 C; 210/198.2, 502.1, 635, 656

[56] References Cited

U.S. PATENT DOCUMENTS 3,212,854 10/1965 Betts et al. ............................. 436/24
4,228,192 10/1980 Sanden .................................. 426/231
4,282,259 8/1981 Wheldon et al. ..................... 426/231
4,302,479 11/1981 Humphrey et al. ................. 426/600
4,447,328 5/1984 Kamiyama et al. ............. 210/656 X

FOREIGN PATENT DOCUMENTS 928672 6/1963 United Kingdom ................ 426/231
431448 6/1975 U.S.S.R. ............................. 426/231

Primary Examiner—David L. Lacey
Assistant Examiner—Jill Johnston
Attorney, Agent, or Firm—Sheldon Palmer

[57] ABSTRACT

An analysis method for hop bittering components which comprises a step of separating and analysing hop bittering components by liquid chromatography, characterized by trapping hop bittering components contained in a sample to be measured in a precolumn consisting of an ester type stationary phase for reversed phase chromatography by passing the sample through the precolumn by means of an acidic aqueous solution containing a polar organic solvent, introducing an eluent for reversed phase chromatography capable of eluting the bittering components into the precolumn, and subjecting the eluate to reversed phase liquid chromatography; and an analysis equipment which is suitable for conducting the above method.

7 Claims, 4 Drawing Sheets

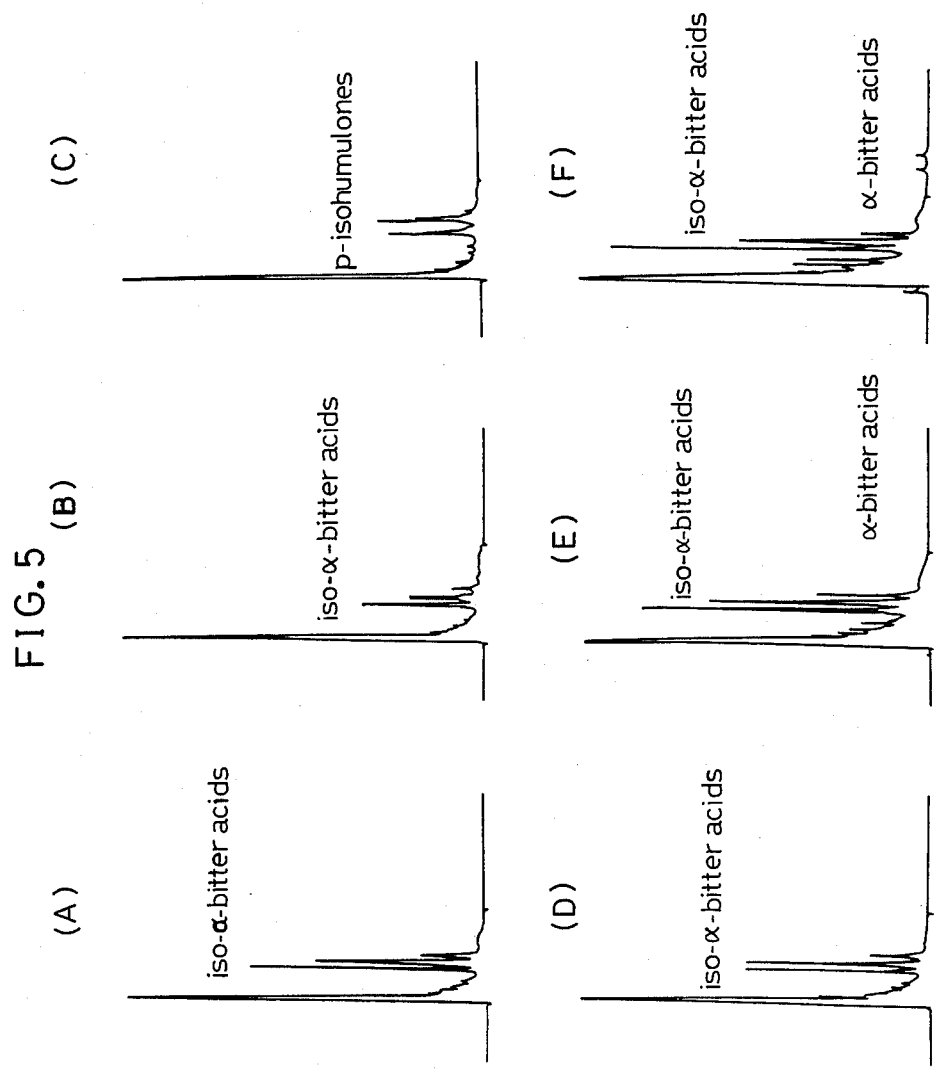

ANALYSIS METHOD FOR HOP BITTERING COMPONENTS

BACKGROUND OF THE INVENTION

1. Field of the Invention

The present invention relates to separation and analysis of hop bittering components (bittering components originated from hops). More particularly, the present invention relates to an analysis method and an analysis equipment for separating and analysing bittering components contained in rough hops, hop products or hop drinks such as beer, by simple operation and with high precision.

2. Description of the Prior Art

Bitterness of hop drinks such as beer, results from bittering components originated from hops, and the bittering components are understood to be consisting of humulones ($\alpha$-acids), such as humulone, cohumulone, adhumulone, etc., and isohumulones (iso-$\alpha$-acids), such as isohumulone, isocohumulone, isoadhumulone, etc. Analysis of these bitter components is of great significance for the control of beer manufacturing process, especially beer brewing process, and the control of quality of the final beer. Analysis of the above-mentioned components is important also in respect of the control of bitterness of other hop drinks, the control of different bittering components due to the difference in the growing district and the harvesting season of the rough hops and accordingly the control of purchase and receiving of the rough hops.

Hitherto, analysis of such bittering components, especially of the bittering components in hop drinks such as beer, has been performed according to a process wherein a sample to be tested is subjected to extraction treatment with isooctane or methanol under acidic condition by hydrochloric acid, the organic phase is evaporated to dryness and then diluted with methanol to a prescribed volume, and the resulting solution is subjected to ion-exchange chromatography or reversed phase chromatography to separate, analyse and estimate the bittering components [M. Verzele, C. Dewaele: ASBC. J. 39, No. 2, 1980 and J. Chromatogr., 197. 189. 1980]. Without such extraction treatment, separation of bittering components was hindered by coloring matters, protein, etc. coexisting in the sample, and it was difficult to estimate the bittering components by liquid chromatography.

However, the conventional method as mentioned above involves problems that (1) operations for the extraction are troublesome, (2) about 1 hour is requested for the preparation of one sample, (3) the large amount of extracting solvent consumed results in the high cost of analysis, (4) errors in the operations for extraction are gross, and so forth.

In view of such problems, the present invention has been made to provide an analysis method and an analysis equipment for separating and analysing bittering components in hops, hop products and hop drinks containing other coexisting components, by rapid and simple operation and with high precision, without effecting any operation for the extraction.

SUMMARY OF THE INVENTION

The inventors of the present invention have made investigation on means for removing coexisting components which might hinder separation of bittering components, in flow-lines of liquid chromatography, particularly on setting of a precolumn for removing the coexisting components. As a result of such investigation, it has been found that the bittering components are trapped selectively in a precolumn when an ester type separation column of reversed phase chromatography, which is hitherto known as one of separation columns for reversed phase, is used as a precolumn, in combination with a specific sample preparation for mobile phase. The present invention has been completed on the basis of such findings, by making further investigations.

Thus, according to the present invention, an analysis method for hop bittering components which comprises a step of separating and analysing hop bittering components by liquid chromatography, characterized by trapping hop bittering components contained in a sample to be measured in a precolumn consisting of an ester type stationary phase for reversed phase chromatography by passing the sample through the precolumn by means of an acidic aqueous solution containing a polar organic solvent, introducing an eluent for reversed phase chromatography capable of eluting the bittering components into the precolumn, and subjecting the eluate to reversed phase liquid chromatography, is provided. Further, an analysis equipment suitable for performing such analysis method is provided according to the present invention.

According to the method and equipment of the present invention, hop bittering components ($\alpha$-acids, iso-$\alpha$-acids and $\beta$-acids) of hop drinks such as beer can be separated and analysed efficiently by introducing the hop drinks directly into the flow-lines of liquid chromatography. The method and equipment, not requiring any complex operation for extraction as required in the conventional method, have merits that the operations for analysis are simple and can be performed in a short time and moreover the errors due to the operation for extraction are dissolved. Further, they are advantageous also in respect of the cost for analysis. Therefore, the method and equipment of the present invention are useful for analysis of not only hop drinks but also various samples whose hop bittering components come into question.

BRIEF DESCRIPTION OF THE DRAWINGS

FIG. 5 is chromatogram diagrams showing the results of analysis of bittering components obtained by the method of the present invention with respect to various beers.

DETAILED DESCRIPTION OF THE PREFERRED EMBODIMENT

Figure 1:
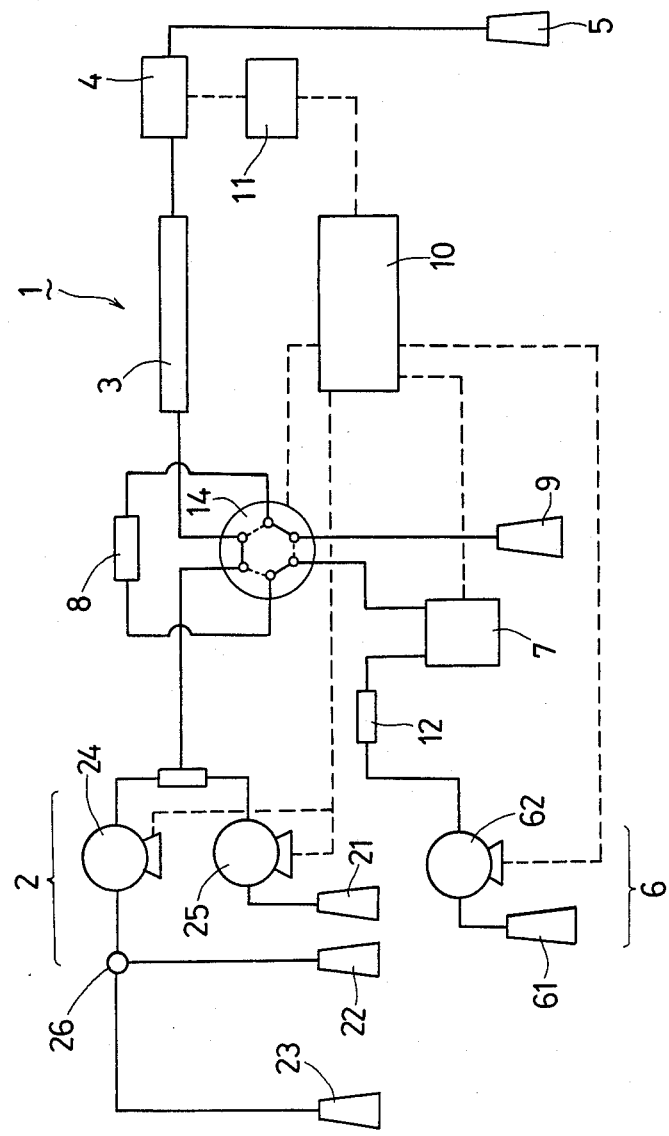
FIG. 1 is a schematic diagram showing the set-up of an equipment of the present invention.

As samples to be analysed according to the present invention, there can be mentioned rough hops, hop products such as hop powder and hop extracts, hop drinks such as wort and beer, and others. When the sample is a liquid matter such as wort or beer, it is possible to perform the analysis in a significantly reduced time compared with the conventional method, by introducing the sample directly into the precolumn without effecting any pretreatment such as extraction. When the sample is a solid matter such as hops, hop powder, hop pellets or the like, the analysis can be performed in a shortened time by introducing the extract obtained by extracting the solid sample with a solvent such as benzene, toluene or the like, directly or after dilution with a hydrophilic solvent such s methanol into the precolumn, without necessitating any complicated and time-consuming operations for extraction as required in the conventional ASBC method.

As the precolumn used in the present invention, it is necessary to select an ester type one among the so-called stationary phases for reversed phase liquid chromatography, for example, an acrylate type stationary phase, sulfonated polystyrene, dextran, polyacrylamide, or the like. Acrylate type stationary phases as preferred. The most preferable precolumn is one using a stationary phase comprising a tetramethylolmethane triacrylate type resin. Columns comprising sucy stationary phase are available, for example, under the name Shim-pack SPC-RP1 (from Shimadzu Corporation, Japan).

As the solution used for the trapping of bittering components in the above-mentioned precolumn, an acidic aqueous solution containing a polar organic solvent is selected. Aqueous solutions having a pH of 2–4 containing approximately 20–40% by volume of a lower alcohol, such as methanol or ethanol, or acetonitrile are suitable as the solution, and it is preferable to use an aqueous phosphoric acid solution containing approx. 20–30% by volume of methanol. Too much polar organic solvent or too low pH value is not favorable, since it makes not only the impurities but also the bittering components per se easily eluted. On the other hand, too less polar organic solvent or too high pH value is also not favorable, since it makes not only the bittering components but also the impurities easily trapped. Thus, the most preferable treatment liquor is an aqueous methanol solution containing approx. 20% by volume of methanol and having a pH of 2.5–2.6.

By passing a sample to be measured through the above-mentioned precolumn using the above-mentioned treatment liquor as medium, the bittering components are retained in the precolumn efficiently and most of the impurities are eluted and removed. For the elution and removal, a time of approx. 2 to 5 minutes is sufficient.

The bittering components trapped in the precolumn are then subjected to liquid chromatography. It is performed by introducing to the column a liquor which is capable of eluting the bittering components trapped in the precolumn and acting as a suitable mobile phase for the separation column for the subsequent chromatography, and transferring the eluate from the column into a separation column to separate the bittering components. As such mobile phase, polar mobile phases containing an alkylammonium are suitable. Particularly, an aqueous methanol or acetonitrile containing a minor amount of tetraethylammonium hydroxide or its salt is used preferably. As a more concrete embodiment, a solution obtained by dissolving 10–20 m mol of tetraethylammonium hydroxide in an aqueous methanol containing 20–25% by volume of water can be mentioned. By introducing such polar mobile phase, the bittering components in the precolumn are rapidly eluted and provided for the separation and analysis in a separation column.

By the way, as the separation column, usual separation columns for reversed phase chromatography are used, and ODS type columns which are available, for example, under the name Shim-pack CLC ODS/H (from Shimadzu Corporation, Japan), are suitable.

On carrying out the method of the present invention as mentioned above, it is preferred in respect of analysis operation and automation to perform the trapping and elution at the precolumn and the separation and analysis of the bittering components by setting two flow-lines, one for the pretreatment and one for the separation and analysis, and linking the two flow-lines. From such point of view, the present invention provides also an analysis equipment for hop bittering components which comprises a flow-line for liquid chromatography having a supply portion for a polar mobile phase containing an alkylammonium, a separation column for reversed phase chromatography and a detector portion, being connected in this order; a flow-line for pretreatment having a supply portion for an acidic aqueous solution containing a polar organic solvent, an introduction portion for a sample containing hop bittering components and a precolumn comprising an ester type stationary phase for reversed phase chromatography, being connected in this order; and a switching flow-line capable of introducing the polar mobile phase into the precolumn on the flow-line for pretreatment and transferring the polar mobile phase to the separation column for reversed phase chromatography through said precolumn, being provided on the flow-line for liquid chromatography between the supply portion for the polar mobile phase and the separation column for reversed phase chromatography. In such equipment, the supply portion for the polar mobile phase may be one for gradient elution, and a column for preliminary cutting of impurities contained in the mobile phase, the acidic solution or the sample to be measured (the so-called pre-cut-column) may be set in the upper stream of each flow-line.

The present invention is explained further in detail, by giving Examples which however shall never limit the ambit of the invention.

EXAMPLE 1

FIG. 1 is a schematic diagram showing an automatic analysis equipment of bittering components of the present invention. In this figure, an automatic analysis equipment (1) is composed basically of a flow-line for liquid chromatography (HPLC) connecting a supply portion for a polar mobile phase (2), a separation column for reversed phase chromatography (3) and a detector (4: a UV monitor) and a flow-line for pretreatment connecting a supply portion for an acidic aqueous solution (6), an introduction portion for a sample to be measured (7: an autoinjector SIL-6A) and a precolumn (8). The supply portion for a mobile phase (2) comprises a supply portion for gradient elution capable of supplying a mobile phase consisting of 77.5 V% of methanol, 22.5 V% of water, 1.79 g of 85% phosphoric acid and 2.959 g of 10% tetraethylammonium hydroxide (21) and a mobile phase consisting of methanol (22) or a mobile phase prepared by adjusting a solution consisting of 77.5% of methanol, 22.5% of water and 2.95 g of 10% tetraethylamine with approx. 1 ml of 42.5% phosphoric acid (pH 4.85) (23) by means of a pump (24) and a pump (25), respectively, in a prescribed ratio. Switching of the mobile phase (22) over the mobile phase (23) or vice versa is effected by a low-pressure flow-line switching valve (26). The separation column for reversed phase chromatography (3) comprises Shim-pack CLC- ODS/H (from Shimadzu Corporation, Japan) and the precolumn comprises Shim-pack SPC-RP1 (from Shimadzu Corporation, Japan) which is a tetramethylolmethane triacrylate type resin stationary phase. The supply portion for an acidic aqueous solution (6) is composed of 0.1% aqueous phosphoric acid solution (pH 2.5) containing 30 V/V% of methanol (61) and a pump (62).

The flow-line for liquid chromatography and the flow-line for pretreatment are linked by a hexagonal electromagnetic valve (14: a high-pressure switching valve), and the polar mobile phase from the supply portion (2) is introduced into the precolumn (8) and transferred therethrough to the separation column (3) as the flow-line is switched over to the broken line side shown in the figure. By the way, (5) and (9) in this figure each show a drain, (11) shows an integrator and (12) shows a pre-cut-column for removing impurities contained in the aqueous solution (61), which comprises the same stationary phase as the precolumn (8). Further, (10) shows a system controller which controls the pumps (24), (25) and (62), the hexagonal electromagnetic valve (14), the flow-pressure flow-line switching valve (26), the supply portion for sample (7), the integrator (11), the detector (4), etc. in the way as described hereinafter.

In the above-mentioned equipment, a sample to be measured, for example, beer is introduced from the supply portion (7) into the flow-line for pretreatment directly, in an amount of 0.1–0.5 ml. The sample is introduced through the flow-line shown by the full line of the hexagonal electromagnetic valve (14) into the precolumn (8) where the bittering components are trapped and other components such as coloring matters, sugars, alcohols, etc. are exhausted fast into the drain (9). After 2–5 minutes, the hexagonal electromagnetic valve (14) is switched over to the flow-line of the broken line and connected with the flow-line for liquid chromatography which is already equilibrated with the polar mobile phase from the supply portion (2). Then, the bittering components trapped in the precolumn (8) are eluted fast and transferred to the separation column (3) where the bittering components are separated into individual constituents. Detection of the resulting fractions is effected around 270–302 nm by the detector (4) and recorded by the integrator (11) where, at the same time, the quantity calculation is effected.

Using the above equipment, analysis of bittering components in a beer on the market was carried out by direct introducing. The temperature of the separation column was adjusted at 50° C., and the flow rate of the polar mobile phase at 1.2–1.5 ml/minute.

Figure 2:
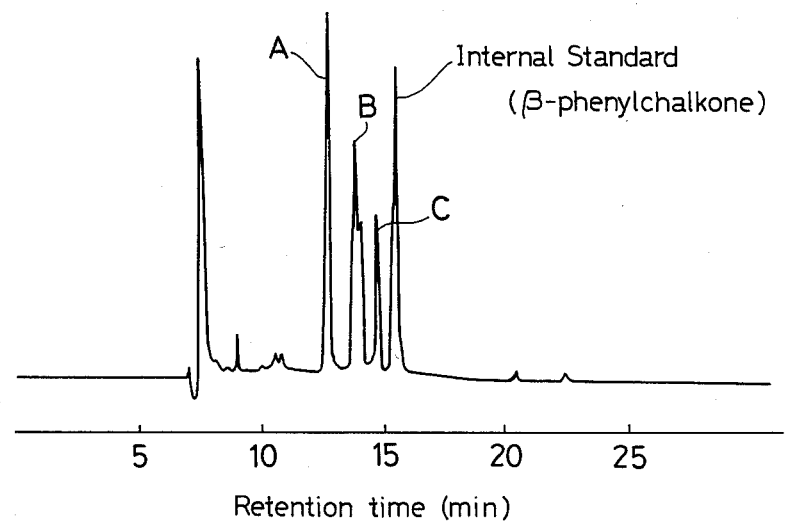
FIG. 2 and FIG. 4 are each a chromatogram diagram showing the peaks of bittering components obtained by the method of the present invention.
Figure 3:
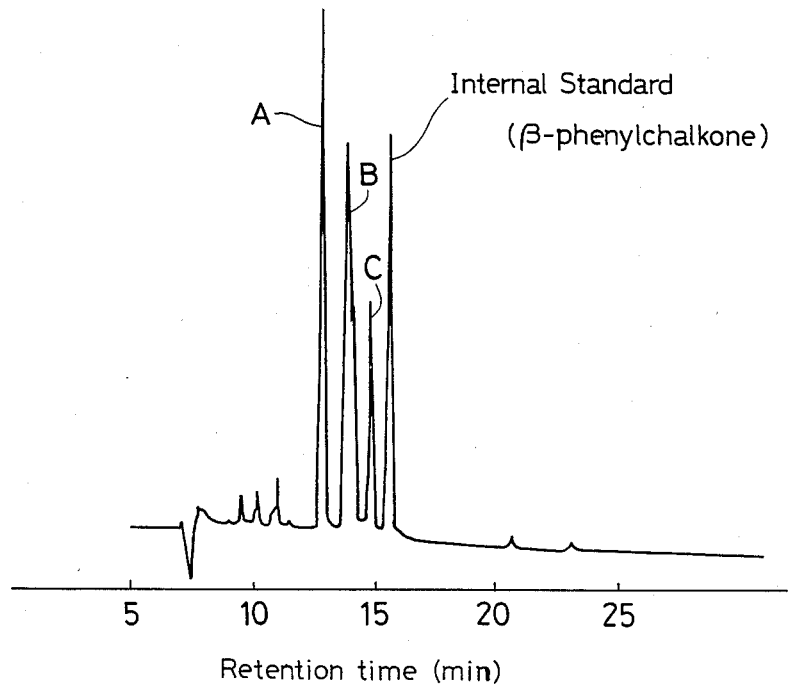
FIG. 3 is a chromatogram diagram showing the peaks of bittering components obtained by the conventional method.
Figure 4:
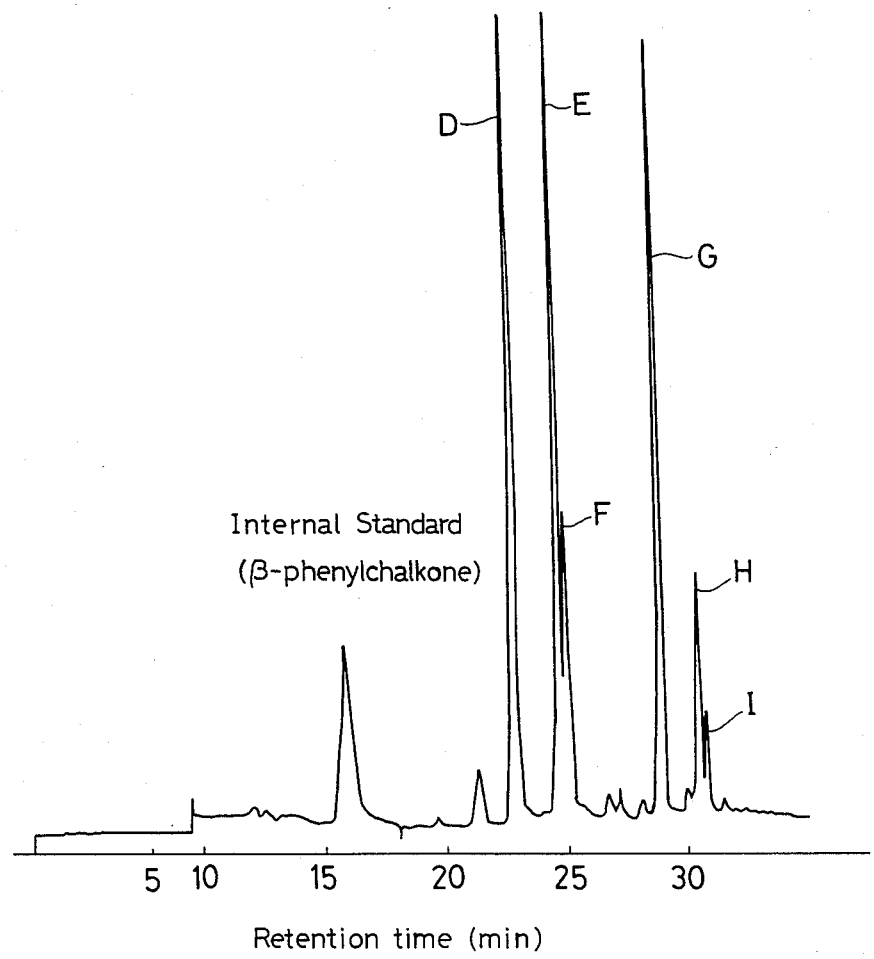

The results so obtained are shown in FIG. 2. Analysis results obtained with the same beer by a conventional method wherein isooctane extraction and reversed phase liquid chromatography is effected in combination are shown in FIG. 3. Further, the results obtained by analysis of bittering components in rough hops are shown in FIG. 4.

In these Figures, A denotes cis- and trans-isocohumulone, B cis- and trans-isohumulone, C cis- and trans-isoadhumulone, D cohumulone, E humulone, F adhumulone, G colupulone, H lupulone and I adlupulone, respectively.

Thus, it is understood that, according to the method of the present invention, bittering components are distinctly separated and their separation and estimation can be performed in a more simple way and with a higher precision as compared with the conventional method.

EXAMPLE 2

Precision of the Automated HPLC Analysis by the invention for Beer and Wort

The fully automated HPLC analysis by column switching of this invention was distinguished by a high level of precision (Table I).

TABLE I

Precision of the automated HPLC analysis by the invention for beer

| n° | Contents (mg/L) | | | |
|---|---|---|---|---|
| | co-[1] | n-[2] | ad-[3] | Total iso-α-acids |
| 1 | 8.0 | 13.2 | 4.5 | 25.7 |
| 2 | 8.0 | 13.2 | 4.5 | 25.7 |
| 3 | 8.0 | 13.2 | 4.4 | 25.6 |
| 4 | 8.0 | 13.3 | 4.4 | 25.7 |
| 5 | 7.9 | 13.3 | 4.4 | 25.6 |
| 6 | 8.0 | 13.2 | 4.4 | 25.6 |
| Mean | 7.98 | 13.23 | 4.43 | 25.65 |
| SD | 0.04 | 0.05 | 0.05 | 0.05 |
| c.v. | 0.5 | 0.4 | 1.1 | 0.2 |

[1]co-; isocohumulone
[2]n-; isohumulone
[3]ad-; isoadhumulone

The relative standard deviations of 6 repeated injections of 120 µl was less than 2% in cases of each component of iso-α-acids, and total iso-α-acids in beer. The same results were attained in cases of iso-α-acids and α-acids for wort (Table II).

TABLE II

Precision of the automated HPLC analysis by the invention for wort

| n° | Contents (mg/L) | | | | | | | |
|---|---|---|---|---|---|---|---|---|
| | co-[1] | n-[2] | ad-[3] | Total iso-α-acids | co-[4] | n-[5] | ad-[6] | Total α-acids |
| 1 | 13.4 | 14.0 | 5.4 | 32.8 | 4.1 | 5.1 | 1.2 | 10.4 |
| 2 | 13.4 | 14.0 | 5.4 | 32.8 | 4.0 | 5.1 | 1.2 | 10.3 |
| 3 | 13.3 | 14.0 | 5.3 | 32.6 | 4.0 | 5.0 | 1.1 | 10.1 |
| 4 | 13.4 | 14.0 | 5.4 | 32.8 | 4.1 | 5.1 | 1.2 | 10.4 |
| 5 | 13.4 | 14.1 | 5.4 | 32.9 | 4.1 | 5.2 | 1.2 | 10.5 |
| 6 | 13.4 | 14.0 | 5.3 | 32.7 | 4.1 | 5.1 | 1.2 | 10.4 |
| Mean | 13.38 | 14.02 | 5.37 | 32.77 | 4.07 | 5.10 | 1.18 | 10.35 |
| SD | 0.04 | 0.04 | 0.05 | 0.10 | 0.05 | 0.06 | 0.04 | 0.14 |
| c.v. | 0.3 | 0.3 | 0.9 | 0.3 | 1.2 | 1.2 | 3.4 | 1.4 |

[1]co-; isocohumulone
[2]n-; isohumulone
[3]ad-; isoadhumulone
[4]co-; cohumulone
[5]n-; humulone
[6]ad-; adhumulone These results confirm tht the fully automated HPLC analysis for hop bittering components in beer and wort is more reproducible, faster, and simpler than other method. The time for sample preparation was reduced to only 5 min. Sample preparation and analysis can be performed every 40 minutes. Consequently, the automated HPLC analysis is suited for routine analyses for monitoring brewing processes in practice.

EXAMPLE 3

Application of the Automated HPLC Analysis by the invention to the Determination of Hop Bittering Components in beers from All over the World A lot of samples available in the world were analysed to obtain information regarding the hops used and to confirm the superiority of the fully automated HPLC by the invention. FIG. 5 shows the examples of typical types of beer [(A) . . . a Japanese beer, (B) . . . an American beer (Light), (C) . . . an American beer, (D) . . . a German beer, (E) . . . a German beer (Pilsner), (F) . . . an English beer (Ale)]. Not only iso-α-acids and α-acids but also ρ-isohumulones can be precisely analysed with comparable precision to the ASBC method.

The claimed method can overcome sample clean-up and enrichment techniques usually encountered with time-consuming and error-prone extraction, evaporation and redissolution steps which normally were performed before the HPLC analysis. One analytical time can be completely performed in 40 min or less to determine all analogs of iso-α-acides, α-acids and β-acids. The recovery and reproducibility of this technique are excellent and are comparable to the prior method with the off-line sample enrichment. The lifetime of the precolumn is sufficiently long that, even after analyses of over 1000 samples in 6 months, the recovery and column efficiency are not reduced. The automated HPLC method of this invention is eminenthly suited to route analyses in the brewery. This method can also be successfully applied to the evaluation of hops and hop products.

What we claim is:

1. In a method for analyzing hop bittering components in hop based beverages which comprises separating hop bittering components from a hop based beverage and analyzing the separated components by liquid chromatography, the improvement comprising trapping the hop bittering components contained in a sample to be measured in a precolumn consisting essentially of an ester type stationary phase for reversed phase chromatography by passing the sample through the precolumn in an acidic aqueous solution containing a polar organic solvent, introducing an eluent for reversed phase chromatography capable of eluting the bittering components into the precolumn, and subjecting the eluate to reversed phase liquid chromatography.

2. The analysis method as claimed in claim 1, wherein the hop based beverage is beer.

3. The analysis method as claimed in claim 1, wherein the sample to be measured is hops or a hop product.

4. The analysis method as claimed in claim 1, wherein the ester type stationary phase for reversed phase chromatography is a stationary phase comprising an acrylate type resin.

5. The analysis method as claimed in claim 1, wherein the ester type stationary phase for reversed phase chromatography is a stationary phase comprising a tetramethylolmethane triacrylate type resin.

6. The analysis method as claimed in claim 1, wherein the acidic aqueous solution containing a polar organic solvent is an aqueous solution having a pH of 2-4 containing approximately 20-40% by volume of a lower alcohol or acetonitrile.

7. The analysis method as claimed in claim 1, wherein the eluent for reversed phase chromatography is a polar mobile phase containing an alkylammonium.

* * * * *